US012611393B2

(12) United States Patent
Berta et al.

(10) Patent No.: US 12,611,393 B2
(45) Date of Patent: Apr. 28, 2026

(54) TREATMENT OF PAIN BY TARGETING NR4A1

(71) Applicant: UNIVERSITY OF CINCINNATI, Cincinnati, OH (US)

(72) Inventors: Temugin Berta, Cincinnati, OH (US); Raquel Tonello, Cincinnati, OH (US)

( * ) Notice: Subject to any disclaimer, the term of this patent is extended or adjusted under 35 U.S.C. 154(b) by 1006 days.

(21) Appl. No.: 17/909,513

(22) PCT Filed: Aug. 31, 2020

(86) PCT No.: PCT/US2020/048760
§ 371 (c)(1),
(2) Date: Sep. 6, 2022

(87) PCT Pub. No.: WO2021/042038
PCT Pub. Date: Mar. 4, 2021

(65) Prior Publication Data
US 2023/0111140 A1    Apr. 13, 2023

Related U.S. Application Data

(60) Provisional application No. 62/893,251, filed on Aug. 29, 2019.

(51) Int. Cl.
*A61K 31/216*       (2006.01)
*A61K 31/121*       (2006.01)
(Continued)

(52) U.S. Cl.
CPC .......... *A61K 31/216* (2013.01); *A61K 31/121* (2013.01); *A61K 31/337* (2013.01); (Continued)

(58) Field of Classification Search
CPC .............. A61K 2300/00; A61K 31/121; A61K 31/216; A61K 31/337; A61K 31/353; (Continued)

(56) References Cited

U.S. PATENT DOCUMENTS

2013/0108602 A1    5/2013  Hedrick et al.
2018/0155292 A1    6/2018  Pettersson

FOREIGN PATENT DOCUMENTS

WO      WO 2005/074969        8/2005

OTHER PUBLICATIONS

Quintao et al. "Pharmacological Treatment of Chemotherapy-Induced Neuropathic Pain: PPARγ Agonists as a Promising Tool", Frontiers in Neuroscience, Aug. 28, 2019 (Aug. 28, 2019), vol. 13, pp. 1-13, p. 4; 17 pages.

(Continued)

*Primary Examiner* — Savitha M Rao
(74) *Attorney, Agent, or Firm* — Wood Herron & Evans LLP

(57)    ABSTRACT

The present invention involves a method of treating pain. The method treats a patient having post-operative pain or chemotherapy induced neuropathic pain, and it involves a) assessing the patient to determine if they are experiencing post-operative pain or chemotherapy induced neuropathic pain, and if such pain is diagnosed; b) administering to the patient a therapeutically effective amount of an agonist for the nuclear receptor subfamily 4, group A, member 1 (NR4A1). In one embodiment, the agonist is selected from the group consisting of Cytosporone B, Ethyl 2-[2,3,4-trimethoxy-6-(1-octanoyl)-phenyl] acetate (TMPA), 1,3,7-trihydroxy-2,4-diprenylxanthone (CCE9), 1-(3,4,5-trihydroxyphenyl)-nonan-1-one (THPN), DIM-C-pPhOCH3 (C-DIM-5), 1,1-bis(3'-indolyl)-1-(phenyl)methane (DIM-C-Ph) and 1,1-bis(3'-indolyl)-1-(p-anisyl)methane (DIM-C-pPhOCH_3).

12 Claims, 21 Drawing Sheets

(51) Int. Cl.

| | |
|---|---|
| *A61K 31/337* | (2006.01) |
| *A61K 31/353* | (2006.01) |
| *A61K 31/404* | (2006.01) |
| *A61P 25/02* | (2006.01) |
| *A61P 25/04* | (2006.01) |

(52) U.S. Cl.
CPC .......... *A61K 31/353* (2013.01); *A61K 31/404* (2013.01); *A61P 25/02* (2018.01); *A61P 25/04* (2018.01)

(58) Field of Classification Search
CPC ....... A61K 31/404; A61K 45/06; A61P 25/02; A61P 25/04
See application file for complete search history.

(56) References Cited

OTHER PUBLICATIONS

International Search Report and Written Opinion for PCT/US20/48760 dated Nov. 30, 2020, 7 pages.

Experimental design

Experimental design

FIG. 6A

TREATMENT OF PAIN BY TARGETING NR4A1

CROSS REFERENCE TO RELATED APPLICATIONS

This application claims priority to International Application No. PCT/US20/048760, filed Aug. 31, 2020, which claims priority to U.S. Provisional Application Ser. No. 62/893,251, filed Aug. 29, 2019, which applications are hereby incorporated by reference in their entirety.

STATEMENT REGARDING FEDERALLY FUNDED RESEARCH OR DEVELOPMENT

This invention was made with government support under R21 NS106264 awarded by the National Institutes of Health. The U.S. Government has certain rights in the invention.

TECHNICAL FIELD

The present invention relates to methods of preventing and treating pain. More specifically, this invention relates to methods targeting the nuclear receptor NR4A1.

BACKGROUND OF THE INVENTION

Globally, more than 320 million people have surgery each year with many patients enduring severe post-operative pain, even after surgery widely considered to be minor. Inflammatory responses are essential for tissue repair and pain after surgery, but failure to terminate these responses can result in severe and chronic pain. It is estimated that 10% of all patients who had surgery develop chronic pain. Despite decades of research, management of post-operative pain still relies on opioids contributing to their widespread and misuse.

Although neuropathological changes in response to surgery are considered the provocative processes for the development of pain after surgery, accumulating evidence has demonstrated an important role for local inflammation, characterized by infiltration of neutrophils, macrophages and other immune cells, in the development and progression of post-operative pain.

In addition, up to 80% of patients undergoing cancer treatment often experience chemotherapy-induced neuropathic pain (CINP), for which there is no FDA-approved drug. There have been many studies which investigated the effects of opioids, antiepileptics, and antidepressants on CINP, but clinical results have been disappointing. Although the exact mechanisms underlying paclitaxel-induced neuropathic pain remain incompletely known, there are preclinical lines of evidence indicating that immune cells in dorsal root ganglia play critical roles in the development and progression of chemotherapy-induced pain-like behaviors (i.e., mechanical and cold allodynia), which are reminiscent of its clinical symptoms. Interestingly, it has been reported that various chemotherapy agents induce the infiltration of monocytes into the dorsal root ganglia (DRGs) and sciatic nerve, where they differentiate into inflammatory macrophages and contribute to pain-like behaviors in several animal models of CINP, including in animals receiving the commonly used chemotherapeutic drug paclitaxel. A need still exists for methods to resolve and/or manage post-operative pain or CINP.

SUMMARY OF THE INVENTION

The present invention involves a method of preventing and treating pain. The method treats a patient at risk and having severe post-operative pain or chemotherapy induced neuropathic pain, and it involves a) assessing the patient to determine if they are at risk or experiencing post-operative pain or at risk or experiencing chemotherapy induced neuropathic pain, and if such risk or pain are diagnosed; b) administering to the patient a therapeutically effective amount of an agonist for the nuclear receptor subfamily 4, group A, member 1 (NR4A1). In one embodiment, the agonist is selected from the group consisting of Cytosporone B, Ethyl 2-[2,3,4-trimethoxy-6-(1-octanoyl)-phenyl] acetate (TMPA), 1,3,7-trihydroxy-2,4-diprenylxanthone (CCE9), 1-(3,4,5-trihydroxyphenyl)-nonan-1-one (THPN), DIM-C-pPhOCH3 (C-DIM-5), 1,1-bis(3'-indolyl)-1-(phenyl)methane (DIM-C-Ph) and 1,1-bis(3'-indolyl)-1-(p-anisyl)methane (DIM-C-pPhOCH$_3$). In another embodiment, the agonist is Cytosporone B.

In one embodiment, the patient is administered repeated doses of the agonist. In another embodiment, the patient is administered a single dose of the agonist. In one embodiment, the patient is diagnosed at risk or with severe post-operative pain. In another embodiment, the patient is diagnosed at risk or with chemotherapy induced neuropathic pain.

In one embodiment, the agonist is administered by local injection. In another embodiment, the agonist is administered systemically.

In another embodiment, the present invention is a method of preventing pain in a patient who is at risk of developing pain. The method involves assessing the patient to determine if they are at risk of developing pain from a preexisting condition. If such risk is diagnosed the patient is administered a therapeutically effective amount of an agonist for the nuclear receptor subfamily 4, group A, member 1 (NR4A1). In one embodiment, the preexisting condition is selected from the group consisting of previous surgeries, genetic modifications, diseases, psychological state, and combinations thereof.

BRIEF DESCRIPTION OF THE DRAWINGS

The foregoing summary, as well as the following detailed description of preferred embodiments of the application, will be better understood when read in conjunction with the appended drawings.

FIG. 1A illustrates the experimental design depicting the plantar incision and timeline for the behavioral tests. FIG. 1B is a graph showing how, after plantar incision, mice develop mechanical hypersensitivity (assessed by von Frey filaments) and FIG. 1C is a graph showing thermal hypersensitivity (assessed by Hargreaves test). These hypersensitivities are indicative of postoperative pain and resolve in 7 days. n=6 male mice per group, One-way ANOVA, *p<0.05 (Bonferroni).

FIG. 3A shows Mechanical hypersensitivity assessed by von Frey filaments, and FIG. 3B shows thermal hypersensitivity assessed by Hargreaves test. n=9-13 male and female mice per group, Two-way ANOVA, *p<0.05 (Bonferroni).

FIG. 4A is an illustration of the experimental design depicting the plantar incision, and a timeline for the treatments and behavioral tests. FIG. 4B is a graph showing mechanical hypersensitivity as assessed by von Frey filaments before injection of the drug (prevention). FIG. 4C is a graph showing mechanical hypersensitivity as assessed by von Frey filaments after drug injection (acute analgesia). FIG. 4D is a graph showing thermal hypersensitivity as assessed by Hargreaves test before injection of the drug (prevention). FIG. 4E is a graph showing thermal hypersensitivity as assessed by Hargreaves test after drug injection (acute analgesia). Cytosporone B (Cyto B) or vehicle control were administered by intraplantar injections. n=5-6 male mice per group, Two-way ANOVA, *p<0.05 (Bonferroni).

FIG. 5B is a graph showing mechanical hypersensitivity as assessed by von Frey filaments before injection of the drug (prevention), and FIG. 5C is a graph showing mechanical hypersensitivity as assessed by von Frey filaments after drug injection (acute analgesia). FIG. 5D is a graph showing thermal hypersensitivity as assessed by Hargreaves test before injection of the drug (prevention). FIG. 5D is a graph showing thermal hypersensitivity as assessed by Hargreaves test after drug injection (acute analgesia). Cytosporone B (Cyto B) or vehicle control were administered by intraplantar injections. n=5 female mice per group, Two-way ANOVA, *p<0.05 (Bonferroni).

FIGS. 6A and 6B are graphs showing that local injection of NA4A1 agonist fails to resolve postoperative pain in NA4A1 knockout male mice. FIG. 6A is a graph showing mechanical hypersensitivity as assessed by von Frey filaments, and FIG. 6B is a graph showing thermal hypersensitivity as assessed by Hargreaves test. Cytosporone B (Cyto B) or vehicle control were administered by intraplantar injections. n=5 male mice per group, Two-way ANOVA, *p<0.05 (Bonferroni).

FIG. 7A is a graph showing mechanical hypersensitivity as assessed by von Frey filaments. FIG. 7B is a graph showing thermal hypersensitivity as assessed by Hargreaves test. Cytosporone B (Cyto B) or vehicle control were administered by intraperitoneal injections. n=5 male mice per group, Two-way ANOVA, *p<0.05 (Bonferroni).

FIG. 9A shows the time course of mechanical allodynia induced by 2 injections of paclitaxel (2 mg/kg, every other day and indicated by arrows) in wild-type (WT) and Nr4a1−/− mice. n=5 male mice per group, Two-way ANOVA, *p<0.05 compared to baseline and #P<0.05 compared to WT (Bonferroni). FIG. 9B shows the expression levels measured by real-time RT-PCR of neuroinflammatory markers CD68 and GFAP, in DRGs examined on day 14 after paclitaxel treatment. n=3 samples per group, *P<0.05 (t-test) compared to WT.

FIG. 10A shows the time course of mechanical allodynia induced by 4 systemic injections of paclitaxel (2 mg/kg, every other day) in wild-type (WT) with or without Csn-B, which was delivered intrathecally (i.t.) at the as the paclitaxel. n=5 male mice per group, Two-way ANOVA, *p<0.05 compared to vehicle control phosphate buffered saline (PBS) (Bonferroni). FIG. 10B shows the time course of mechanical allodynia in wild-type (WT) with or without Csn-B. Treatments were delivered 14 d after the first delivery of paclitaxel (same delivery protocol as in A) to assess the reversal effect of different doses of Csn-B. n=5 male mice per group, Two-way ANOVA, *p<0.05 compared to vehicle control phosphate buffered saline (PBS) (Bonferroni).

DETAILED DESCRIPTION OF THE INVENTION

Figure 1A:
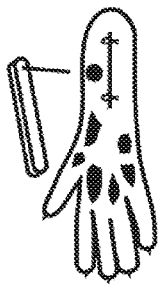
FIGS. 1A-1C show an animal model of post-operative pain.
Figure 1A:
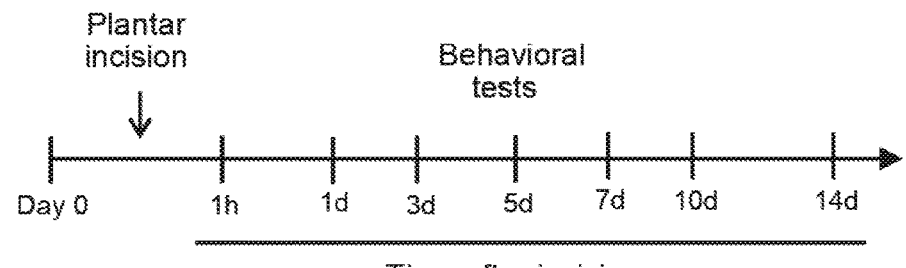
Figure 1B:
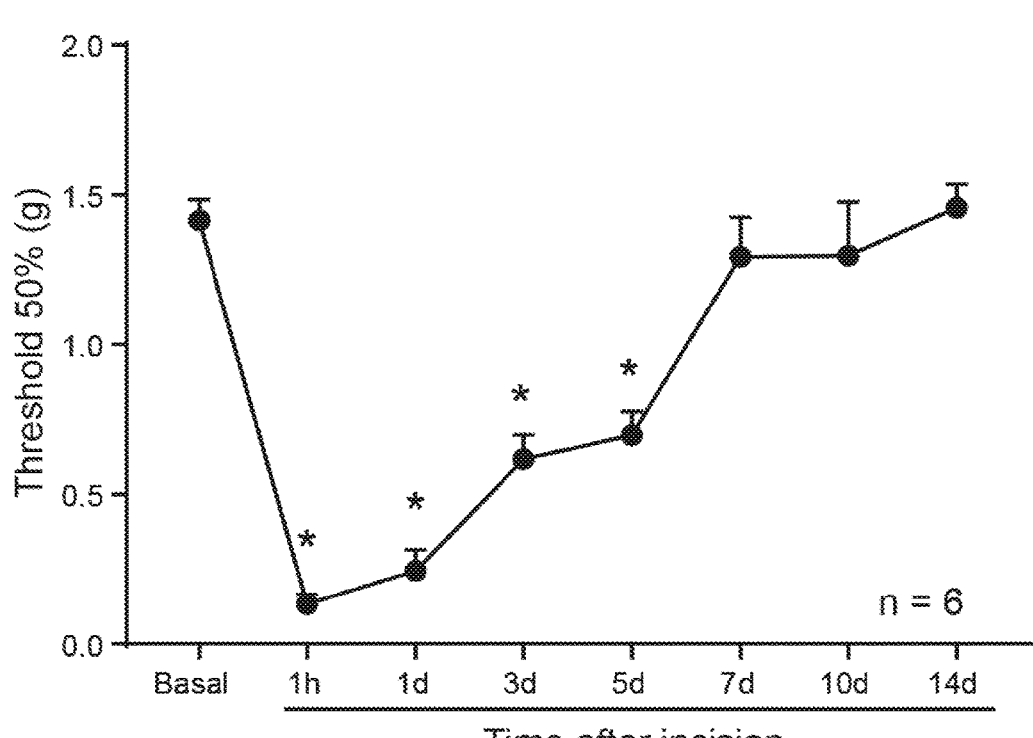
Figure 1C:
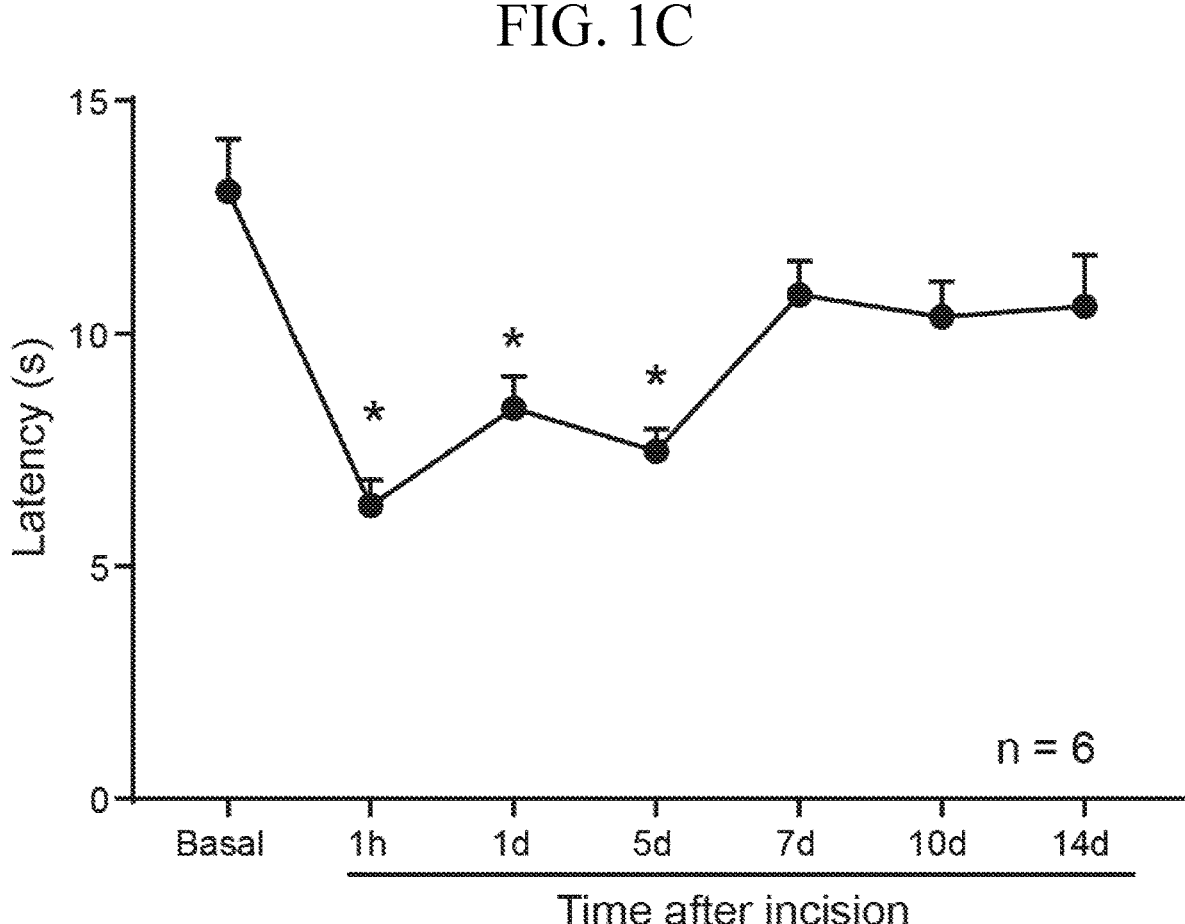

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "agonist", as used herein, refers to a compound that binds to a receptor and has an intrinsic effect, and thus, increases the basal expression or activity of a receptor when it contacts the receptor.

As used herein, the term "locally administered" means that the compound or pharmaceutical composition is administered to the subject at or near a specific site.

As used herein, the term "neuropathic pain" means any pain syndrome caused or caused by primary damage or dysfunction in the peripheral or central nervous system.

As used herein, "post-operative pain" refers to pain arising or resulting from an external trauma or injury such as a cut, puncture, incision, tear, or wound into tissue of an individual (including those that arise from all surgical procedures, whether invasive or non-invasive).

As used herein, "repeated administration" or "repeated dose" refers to administration or dosage for a period of two or more days. At least 2 days, at least 3 days, at least 4 days, at least 5 days, at least 6 days, at least 7 days (one week), or more, or at least 2 weeks, at least 3 weeks, At least 4 weeks (one month) or more, at least 2 months, at least 3 months or more.

As used herein, the terms "treat", "treating" and "treatment" include the eradication, removal, reversion, alleviation, modification, or control of pain after its onset.

As used herein, the terms "prevention", "preventing", "preventive" "prevent" and "prophylaxis" refer to the capacity of a therapeutic to avoid, minimize or difficult the onset or development of a disease or condition before its onset, in this case pain.

"Systemically administered" or "administered systemically" means that the effect associated with administration of the compound or pharmaceutical composition is felt throughout the body, the specific location to which the compound or pharmaceutical composition is administered, or the compound or pharmaceutical composition. Refers to a route of administration of a compound or pharmaceutical composition described herein, such that the article is not limited to a particular means of administration. For example, systemic administration includes, but is not limited to, oral, nasal, parenteral, subcutaneous, intraocular, intradermal, intramuscular, intravenous, intraperitoneal, intrathecal, intravesicular, intraventricular, intraperitoneal, intraparenchymal, transdermal, and transmucosal administration are included.

As used herein, "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, e.g., prevented from happening, or stopped, e.g., terminated, such that the subject no longer experiences the condition. As such, the present method includes both preventing and managing pain.

An "effective amount" or "therapeutically effective amount" of a composition, as used herein, is a predetermined amount calculated to achieve a desired effect.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The nuclear receptor subfamily 4, group A, member 1 (NR4A1) has emerged as a master regulator that controls inflammation and cytokine production in immune cells, including monocytes/macrophages, and its activation promotes the restoration of homeostasis. Mice lacking the expression of NA4A1 develop excessive inflammation and fibrosis, as well as exacerbated disease conditions such as in autoimmune encephalomyelitis and sepsis. The expression and role of NA4A1 in the resolution of pain and the potential of managing either post-operative pain or CINP by small-molecule NA4A1 agonists has been incompletely explored.

We have found that the nuclear receptor NA4A1 is an endogenous inhibitor of inflammatory responses and a therapeutic target for the inflammatory postoperative pain and chemotherapy-induced neuropathic pain. As a result, the present invention uses NR4A1 agonists to treat two general types of pain: inflammatory and neuropathic pain. Any agonist of NA4A1 will be useful. Some specific embodiments of the agonist include Cytosporone B, Ethyl 2-[2,3,4-trimethoxy-6-(1-octanoyl)-phenyl] acetate (TMPA), 1,3,7-trihydroxy-2,4-diprenylxanthone (CCE9), 1-(3,4,5-trihydroxyphenyl)-nonan-1-one (THPN), DIM-C-pPhOCH3 (C-DIM-5), 1,1-bis(3'-indolyl)-1-(phenyl) methane (DIM-C-Ph) and 1,1-bis(3'-indolyl)-1-(p-anisyl) methane (DIM-C-pPhOCH$_3$).

The agonist compounds may be administered locally or systemically. In one embodiment, agonist compounds are administered by local injection. In another embodiment, agonist compounds are administered systemically. In one embodiment, a local injection of the agonist is used to treat postoperative pain and CINP. In another embodiment, a local injection of the agonist is used to treat inflammatory pain, neuropathic pain or both. The agonist may be administered to a patient as a single dose, or it may be administered in repeated doses.

Post-Operative Pain

The present invention has surprisingly found a previously unrecognized role of NR4A1 in regulating inflammatory responses and postoperative pain after surgical incision. As shown in the Examples below, we have found that surgical incision not only induced postoperative pain and infiltration of macrophages, but also resulted in a significant increase of NR4A1 expression levels in the paw of wild-type (WT) mice. Interestingly, NA4A1 KO mice revealed delayed resolution of postoperative pain and increased inflammatory responses in neuronal and skin tissues. Consistently, cultured macrophages from KO mice displayed increased pro-inflammatory responses, whereas inflammatory responses in macrophages from WT mice were significantly reduced when treated with NA4A1 agonists.

Chemotherapy Induced Neuropathic Pain (CINP)

The National Institutes of Health has recently defined the investigation of the biological characteristics underlying the transition from acute to chronic pain as a major challenge that limits our ability to target effective preventive and treatment strategies to patients. Although considerable knowledge is gained about how chronic pain is induced, little is known about how acute pain resolves. As many as 30% of cancer patients develop chemotherapy-induced neuropathic pain (CINP) shortly after the first chemotherapeutic treatment, which then persists and becomes chronic upon the treatment completion, and thus greatly affecting the quality of life of cancer survivors. Chemotherapeutic drugs (e.g., paclitaxel) cause various and distinct cellular and molecular changes in dorsal root ganglia (DRGs) that actively participate to the progression of CINP.

CINP is a dose- and therapy side effect of several chemotherapeutic drugs, including paclitaxel (i.e. Taxol and Onxal). Paclitaxel is one of the most effective chemotherapeutic drugs, widely used for the treatment of solid tumors such as ovarian, breast, and lung carcinoma. Clinical data show that CINP affects 44-98% of cancer patients treated with paclitaxel, which often persists and becomes chronic in cancer survivors. A major challenge in pain care is to prevent the transition from acute to chronic pain. Although considerable knowledge is gained about how chronic pain is induced, little is known about how acute pain naturally resolves. Paclitaxel causes distinct cellular and molecular changes in DRGs that participate to the progression and resolution of CINP. The present invention involves the discovery that the nuclear receptor subfamily 4, group A, member 1 (NR4A1) is an essential factor in DRGs for the proper resolution of neuroinflammation and CINP. We have found that NA4A1 is a novel therapeutic target for the prevention and treatment of chemotherapy-induced neuropathic pain.

NA4A1 controls the proper functions of CD8+ T and Th17 cells, enhances Treg cells, Ly6C-patrolling monocytes and controls anti-inflammatory responses in macrophages. Consequently, mice lacking the expression of NA4A1 develop excessive inflammation and exacerbated in disease conditions such as autoimmune encephalomyelitis and sepsis. Although we have found that NA4A1 is abundantly expressed in human and mouse DRGs, and small molecule NA4A1 agonists have been now identified, the exact cellular expression and role of NA4A1 in the resolution of pain and particularly CINP are completely unknown. As shown in the Examples below, we have found that (1) mice lacking the global expression of NR4A1 have prolonged CINP and increased neuroinflammation in DRGs (e.g., activation of macrophages and excessive cytokine production); (2) different cytokines (e.g., IL-17 and IL-4) and potentially different neuroinflammatory cells sustain the progression and resolution of CINP. Based on our data, we have found that NA4A1 is an essential factor in DRGs for the proper resolution of neuroinflammation and CINP.

Pain Prevention

In another embodiment, the present invention involved using NA4A1 agonists to prevent pain. In one embodiment, the method involves assessing the patient to determine if they are at risk of developing pain from a preexisting condition. If such risk is diagnosed, the patient is administered a therapeutically effective amount of an NA4A1 agonist. Preexisting conditions may include previous surgeries, genetic modifications, diseases, psychological state or combinations thereof. Useful NA4A1 agonists include Cytosporone B, Ethyl 2-[2,3,4-trimethoxy-6-(1-octanoyl)-phenyl] acetate (TMPA), 1,3,7-trihydroxy-2,4-diprenylxanthone (CCE9), 1-(3,4,5-trihydroxyphenyl)-nonan-1-one (THPN), DIM-C-pPhOCH3 (C-DIM-5), 1,1-bis(3'-indolyl)-1-(phenyl)methane (DIM-C-Ph) and 1,1-bis(3'-indolyl)-1-(p-anisyl)methane (DIM-C-pPhOCH$_3$). In one embodiment, the NA4A1 agonist is administered in combination with one or more chemotherapeutic drugs. For example, cytosporone B may be administered in combination with the chemotherapeutic drug paclitaxel to prevent or reduce pain associated with the chemotherapy.

EXAMPLES

Example 1

To investigate the underlying mechanisms of postoperative pain, we adopted a mouse model that is characterized by increased pain sensitivity and macrophage infiltration after a surgical incision made in the plantar aspect of the hind paw. Pain sensitivity and macrophage infiltration were evaluated in NA4A1 knockout (KO) mice. Expression and function of NR4A1 were also evaluated in neuronal and skin tissues, as well as in cultured macrophages.

We used a well-characterized animal model of postoperative pain consisting in plantar incision (FIG. 1). Specifically, FIGS. 1A-1C show an animal model of post-operative pain. FIG. 1A illustrates the experimental design depicting the plantar incision and timeline for the behavioral tests. FIG. 1B is a graph showing how, after plantar incision, mice develop mechanical hypersensitivity (assessed by von Frey filaments) and FIG. 1C is a graph showing thermal hypersensitivity (assessed by Hargreaves test). These hypersensitivities are indicative of postoperative pain and resolve in 7 days. n=6 male mice per group, One-way ANOVA, *p<0.05 (Bonferroni).

Figure 2A:
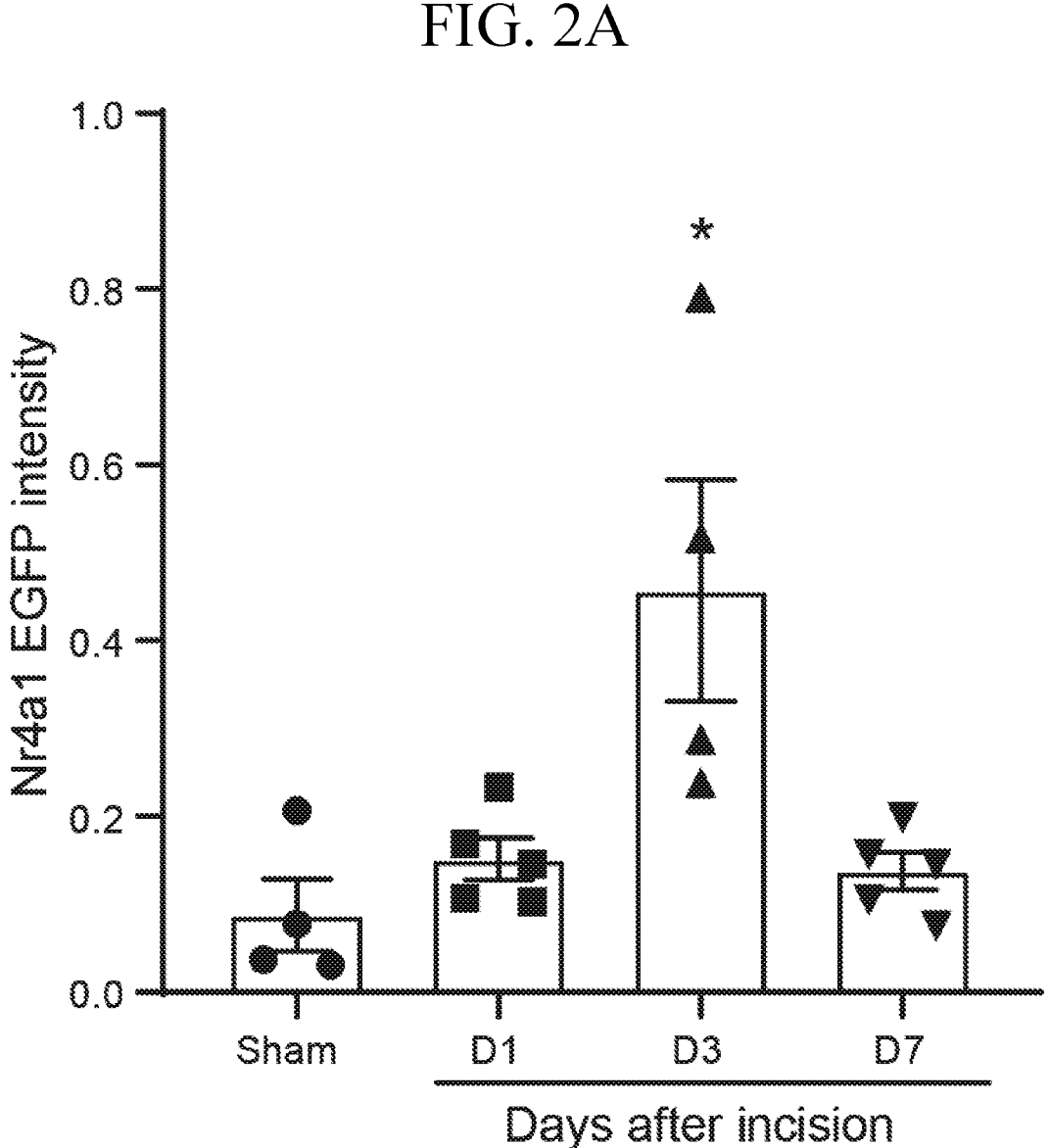
FIG. 2A is a graph showing the quantification of EGFP fluorescent intensity for the induction of NA4A1 in skin tissues (control) vs. 1, 3 and 7 d after plantar incision from the NR4A1-EGFP reporter mice. n=5 mice per time point, One-way ANOVA, *p<0.05 (Bonferroni).
Figure 2B:
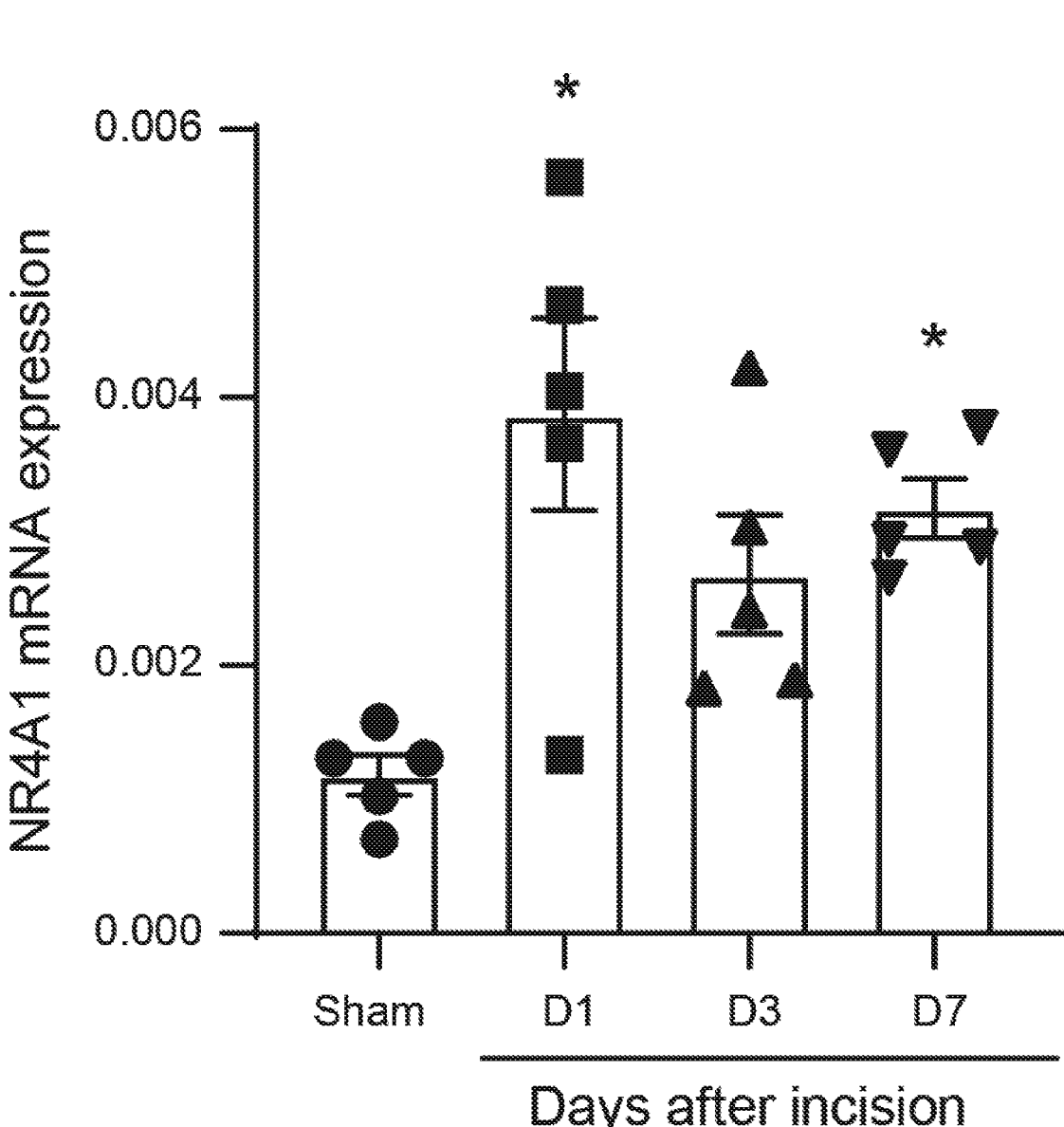
FIG. 2B is a graph showing the quantification by qPCR of NA4A1 mRNA. n=5 mice per time point, One-way ANOVA, *p<0.05 (Bonferroni).

FIG. 2 shows that NA4A1 protein expression levels are increased in cutaneous tissues after this surgery. FIG. 2A is a graph showing the quantification of EGFP fluorescent intensity for the induction of NA4A1 in skin tissues (control) vs. 1, 3 and 7 d after plantar incision from the NR4A1-EGFP reporter mice. n=5 mice per time point, One-way ANOVA, *p<0.05 (Bonferroni). FIG. 2B is a graph showing the quantification by qPCR of NA4A1 mRNA. n=5 mice per time point, One-way ANOVA, *p<0.05 (Bonferroni).

Example 2

Figure 3A:
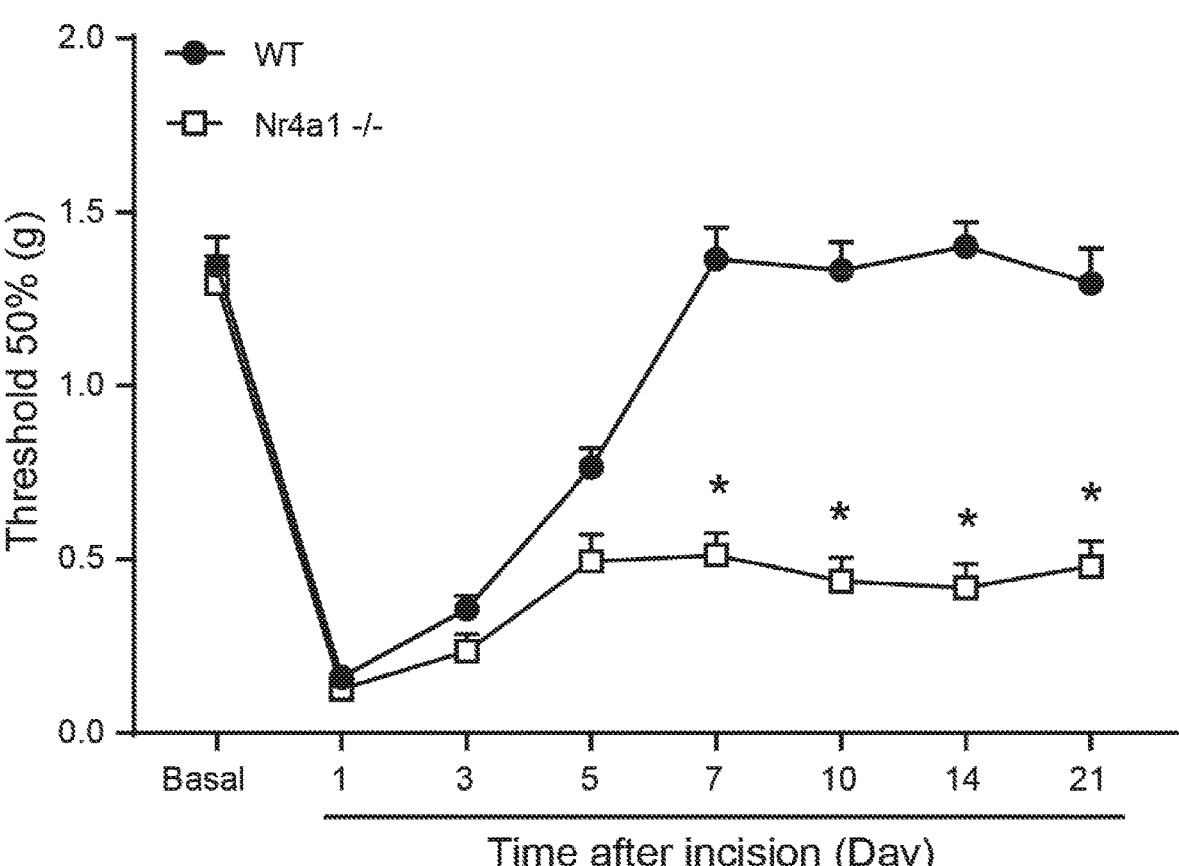
FIGS. 3A and 3B are two graphs showing the impairment of post-operative pain resolution in NA4A1 knockout (Nr4a1−/−) compared to wild-type (WT) mice.
Figure 3B:
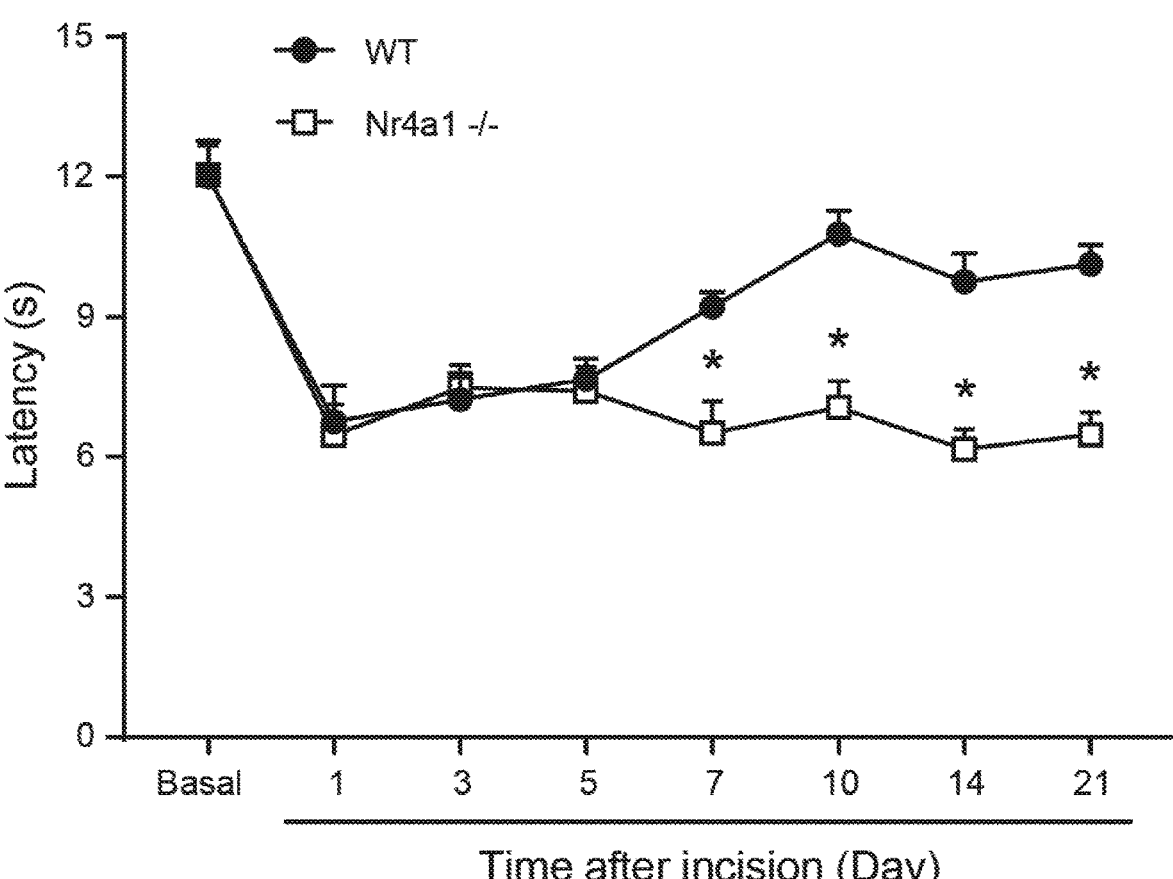

We compared the post-operative pain resolution in NA4A1 knockout (Nr4a1−/−) compared to wild-type (WT) mice. Our results show that mice lacking NA4A1 develop chronic pain. FIGS. 3A and 3B are two graphs showing the impairment of post-operative pain resolution in NA4A1 knockout (Nr4a1−/−) compared to wild-type (WT) mice. FIG. 3A shows Mechanical hypersensitivity assessed by von Frey filaments, and FIG. 3B shows thermal hypersensitivity assessed by Hargreaves test. n=9-13 male and female mice per group, Two-way ANOVA, *p<0.05 (Bonferroni).

Example 3

Figure 4A:
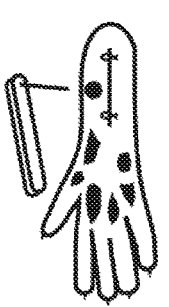
FIGS. 4A-4E show that local intraplantar injection (i.pl.) of NA4A1 agonist accelerates the resolution of postoperative pain in male mice.
Figure 4A:
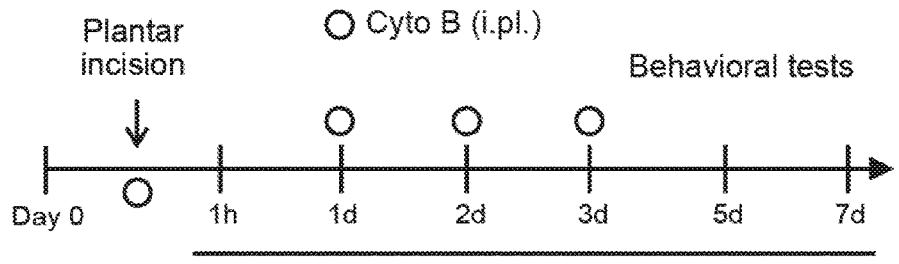
Figure 4B:
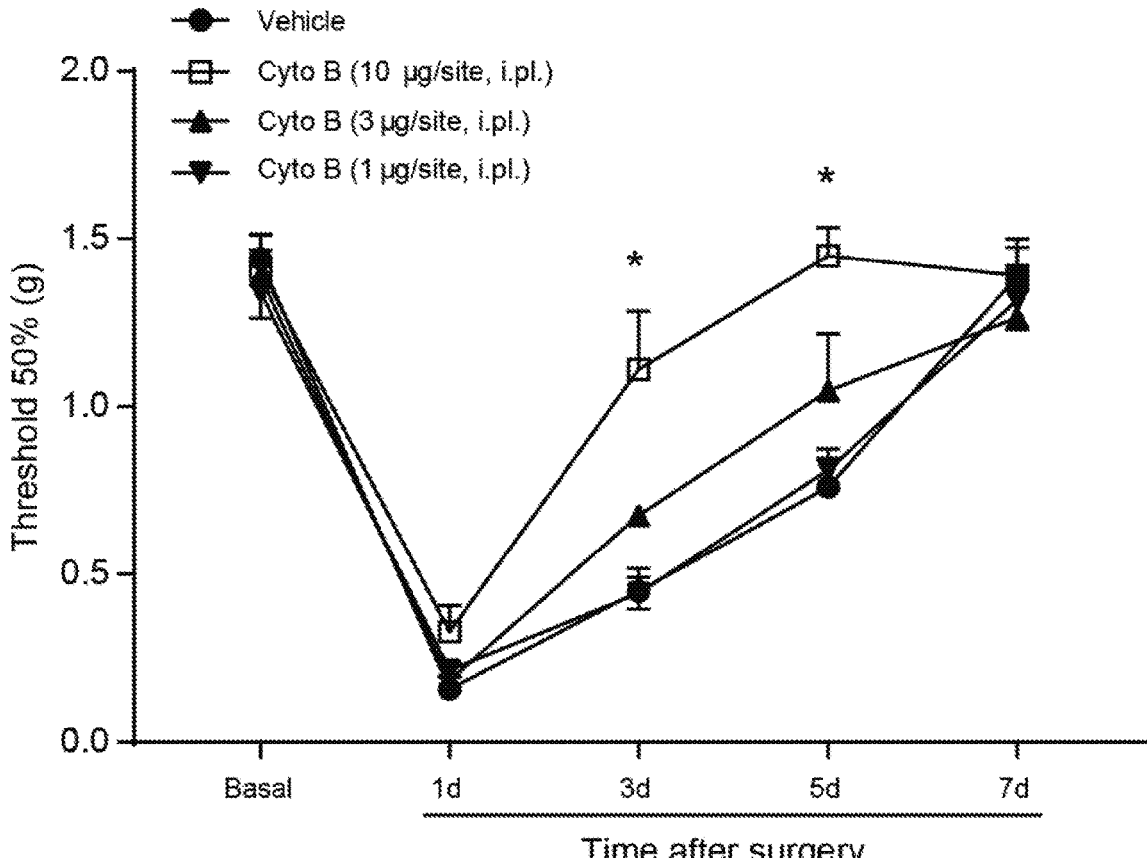
Figure 4C:
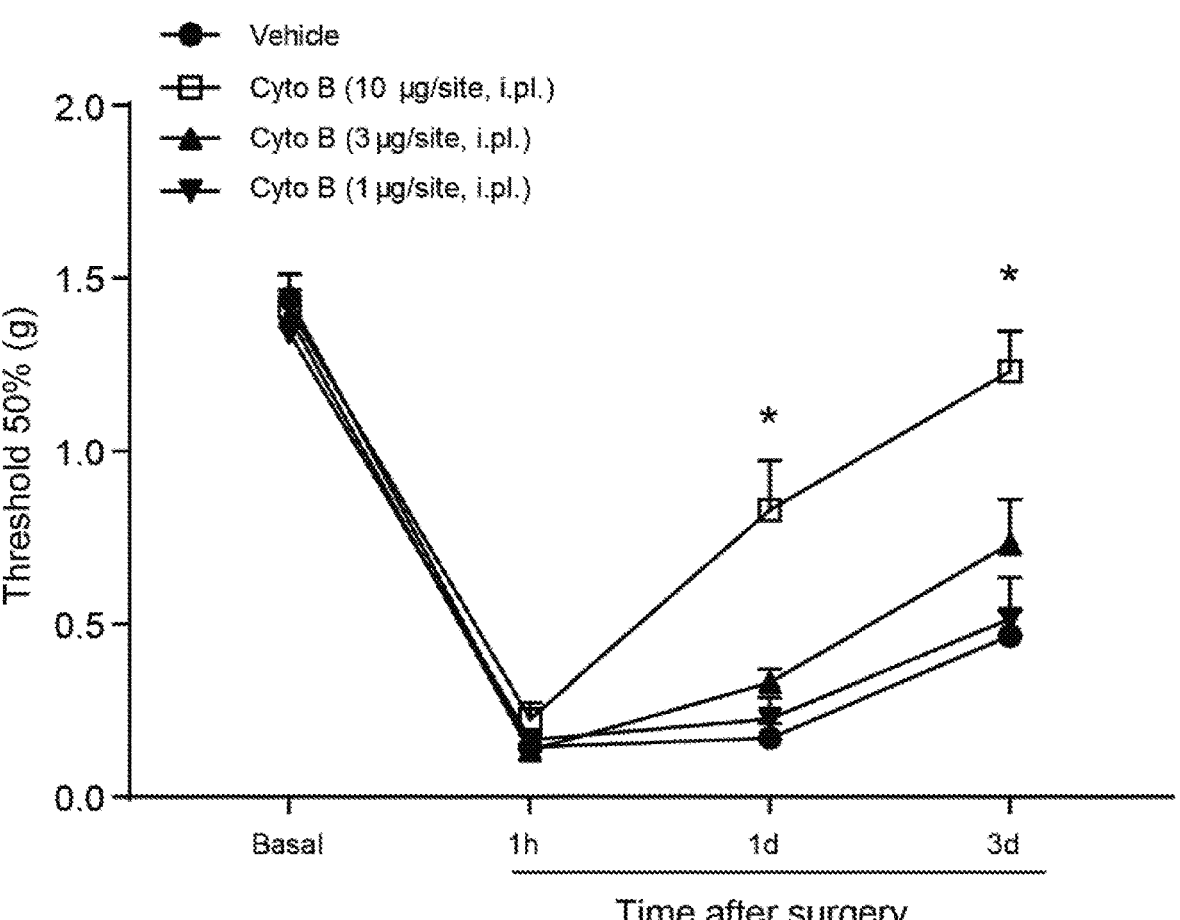

Cutaneous application of an NA4A1 agonist accelerates the resolution of post-operative pain. We conducted a number of tests on male and female mice. FIGS. 4A-4E show that local intraplantar injection (i.pl.) of NA4A1 agonist accelerates the resolution of postoperative pain in male mice. FIG. 4A is an illustration of the experimental design depicting the plantar incision, and a timeline for the treatments and behavioral tests. FIG. 4B is a graph showing mechanical hypersensitivity as assessed by von Frey filaments before injection of the drug (prevention). FIG. 4C is a graph showing mechanical hypersensitivity as assessed by von Frey filaments after drug injection (acute analgesia).

Figure 4D:
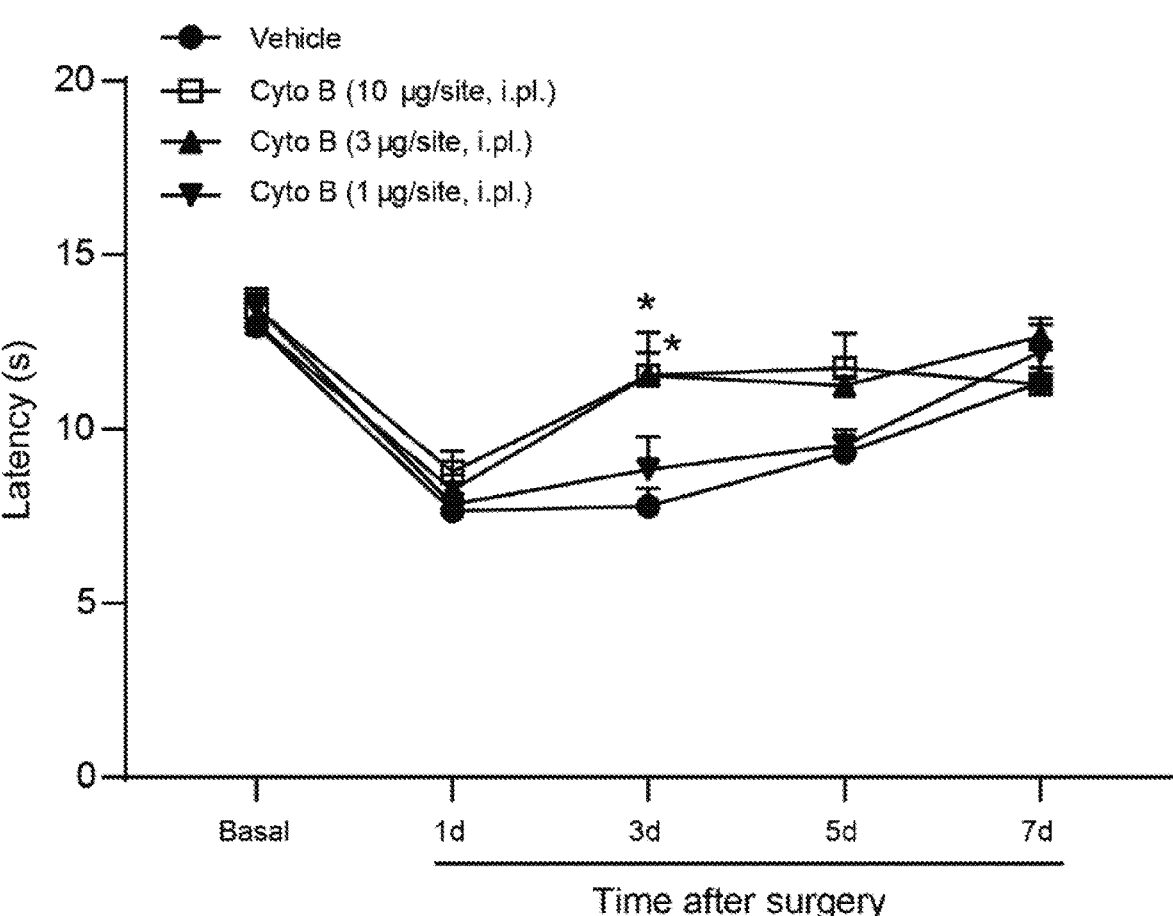
Figure 4E:
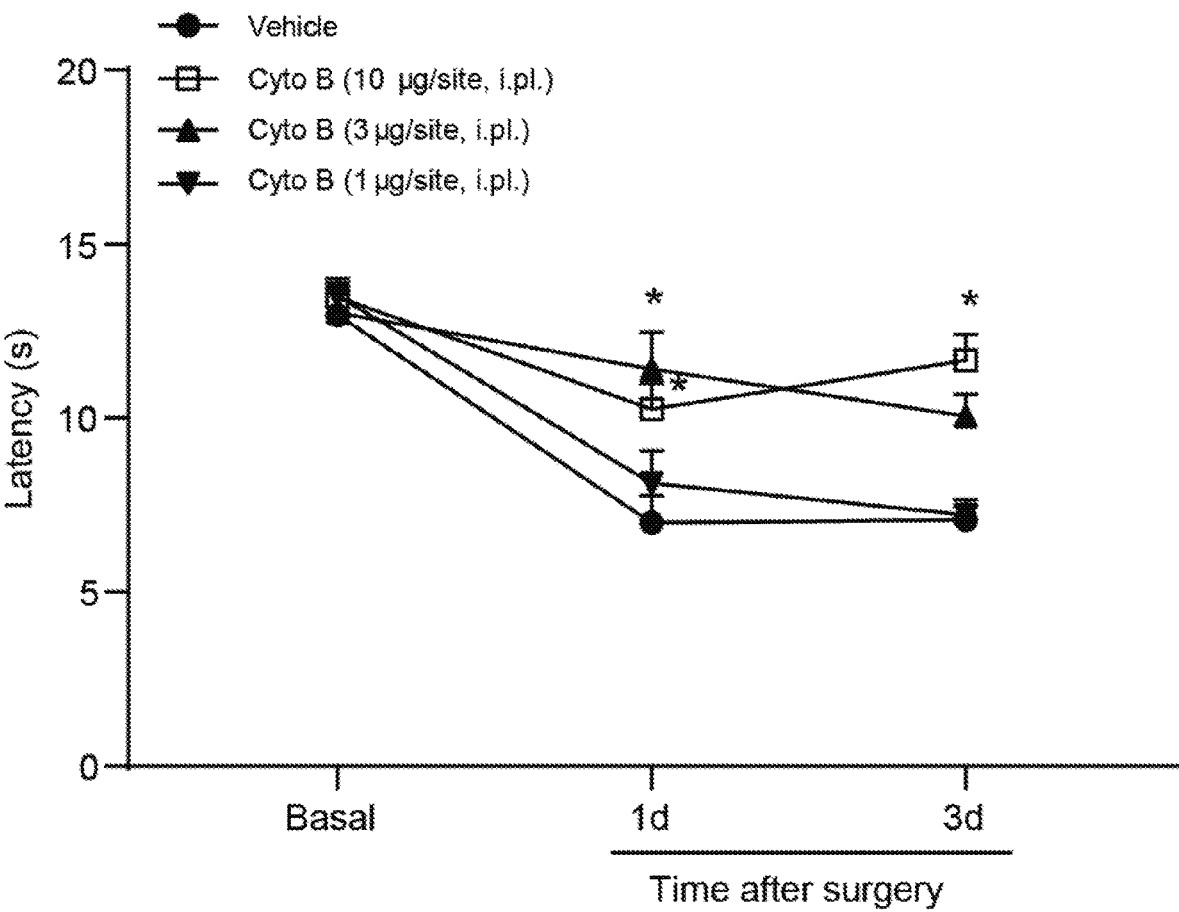

FIG. 4D is a graph showing thermal hypersensitivity as assessed by Hargreaves test before injection of the drug (prevention). FIG. 4E is a graph showing thermal hypersensitivity as assessed by Hargreaves test after drug injection (acute analgesia). Cytosporone B (Cyto B) or vehicle control were administered by intraplantar injections. n=5-6 male mice per group, Two-way ANOVA, *p<0.05 (Bonferroni).

Figure 5A:
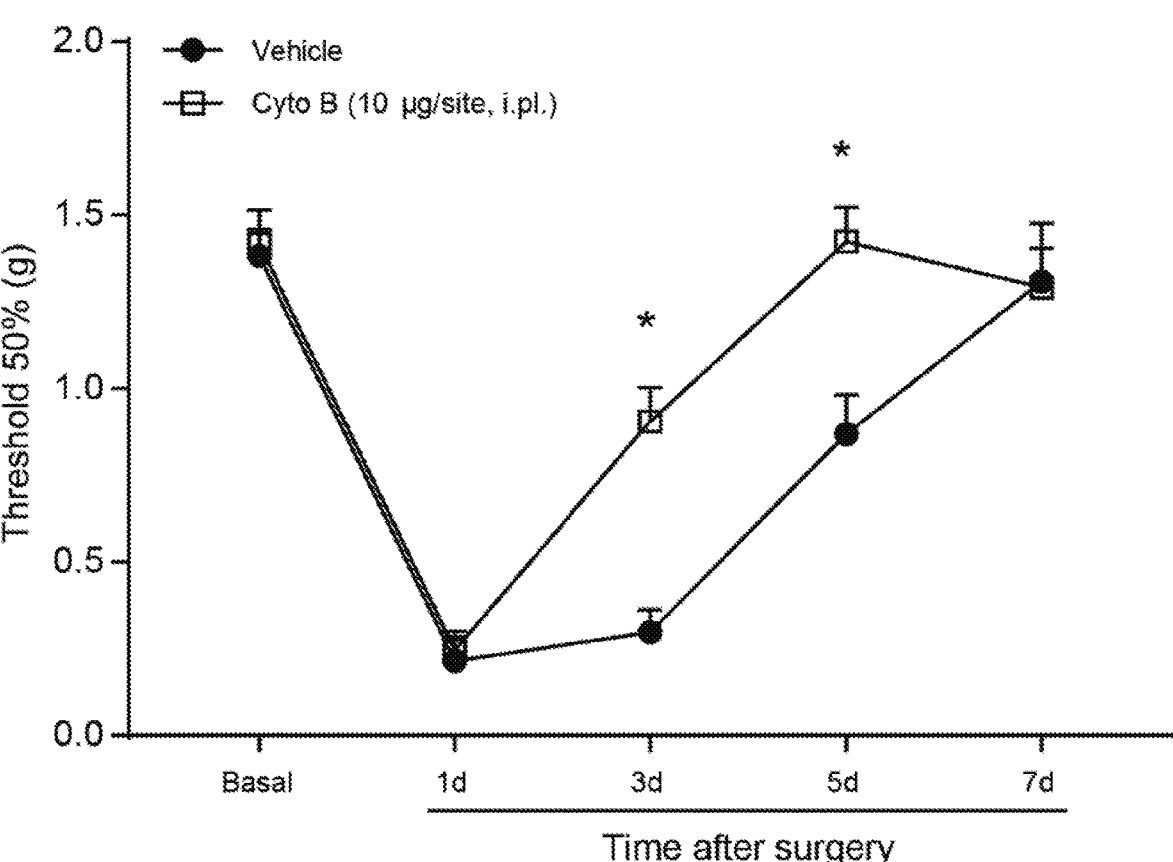
FIGS. 5A-5D show that local injection of NA4A1 agonist accelerates the resolution of postoperative pain in female mice.
Figure 5B:
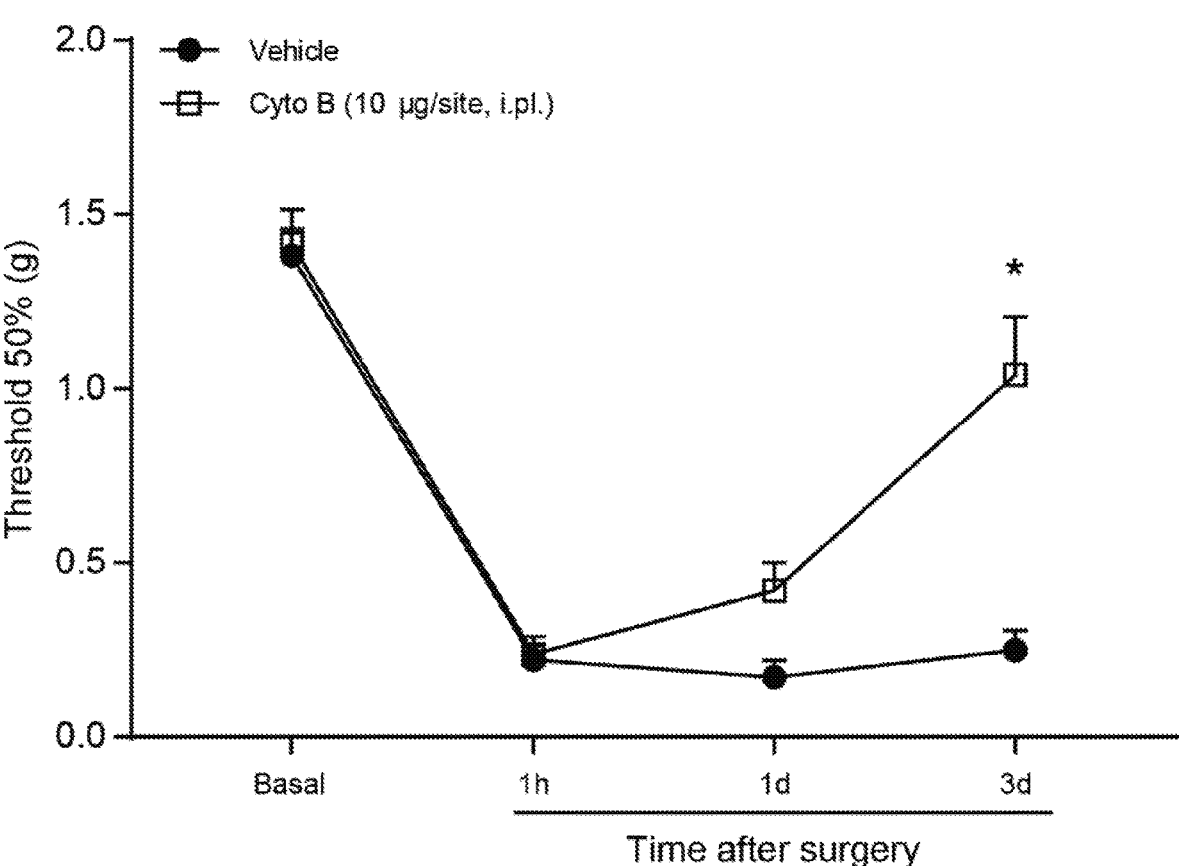
Figure 5C:
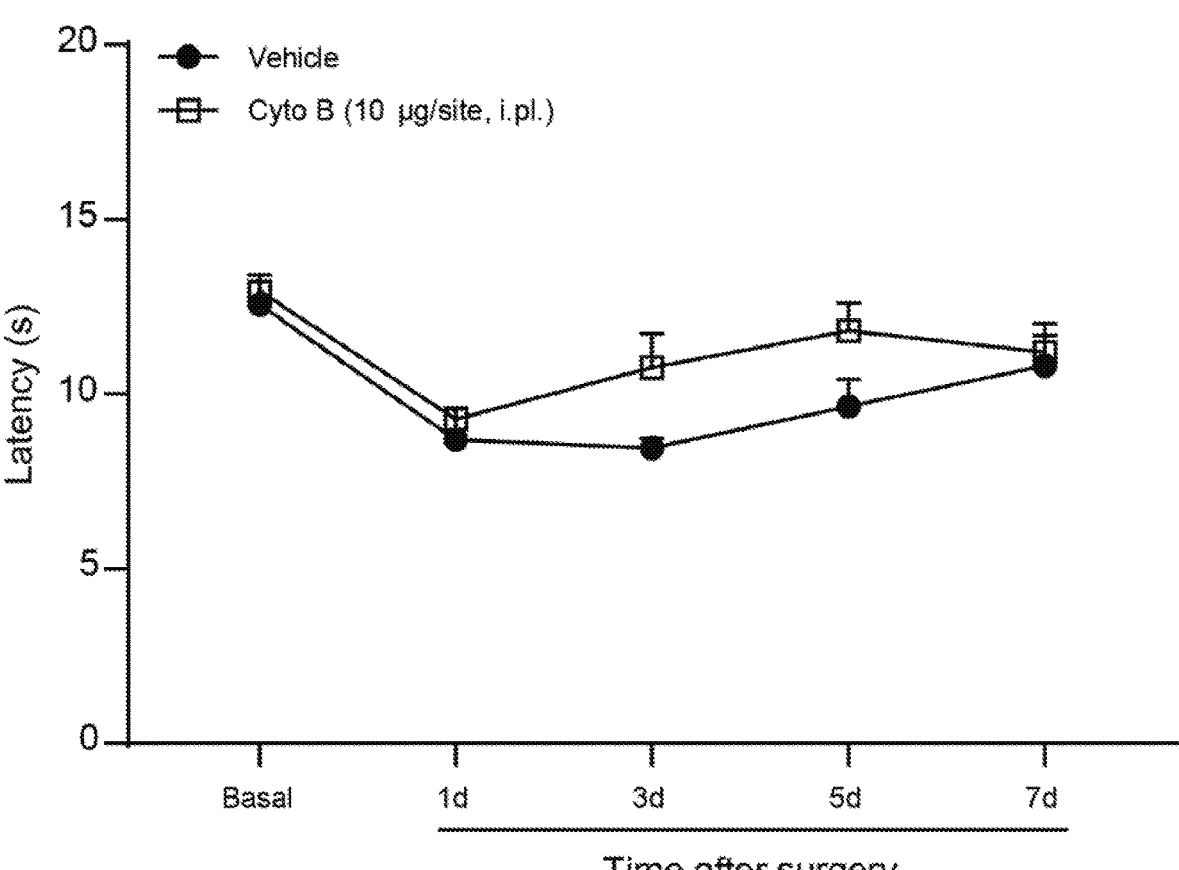
Figure 5D:
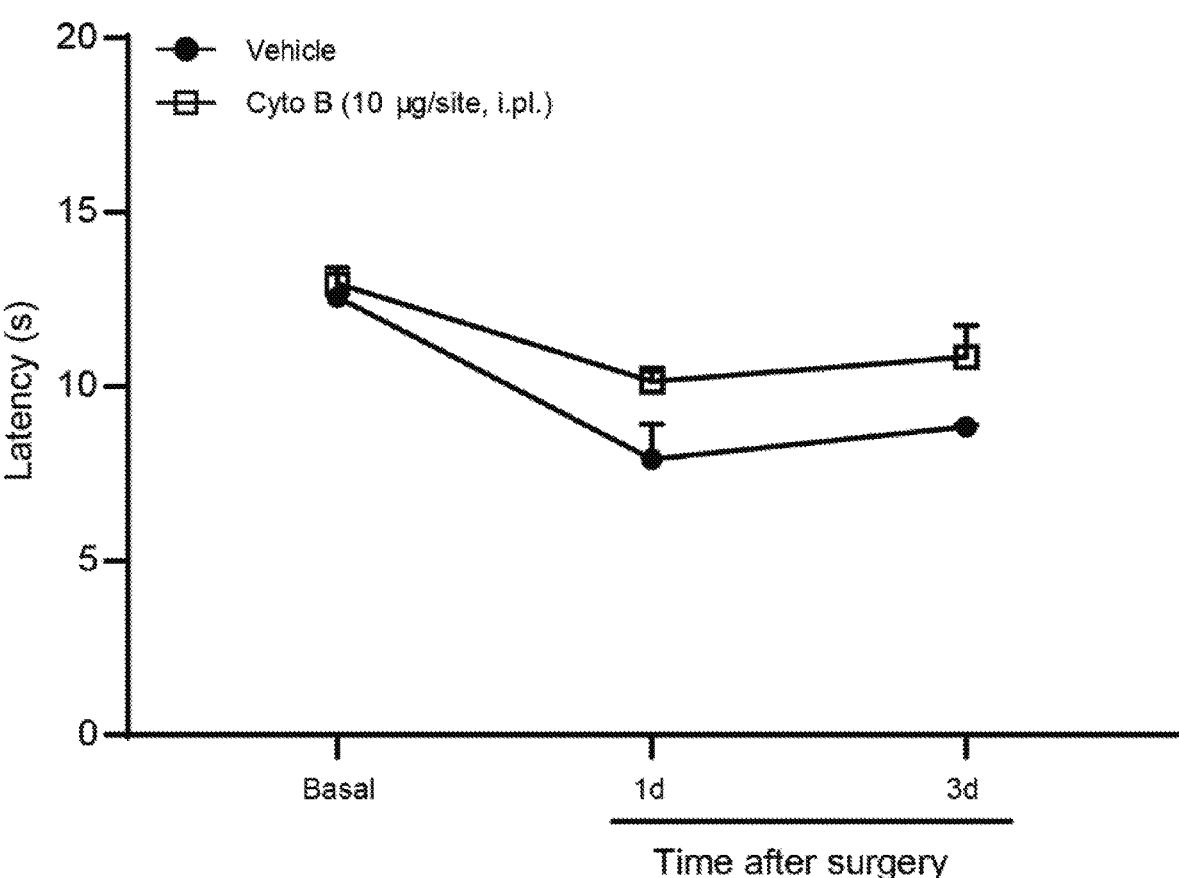

FIGS. 5A-5D show that local injection of NA4A1 agonist accelerates the resolution of postoperative pain in female mice. FIG. 5B is a graph showing mechanical hypersensitivity as assessed by von Frey filaments before injection of the drug (prevention), and FIG. 5C is a graph showing mechanical hypersensitivity as assessed by von Frey filaments after drug injection (acute analgesia). FIG. 5D is a graph showing thermal hypersensitivity as assessed by Hargreaves test before injection of the drug (prevention). FIG. 5D is a graph showing thermal hypersensitivity as assessed by Hargreaves test after drug injection (acute analgesia). Cytosporone B (Cyto B) or vehicle control were administered by intraplantar injections. n=5 female mice per group, Two-way ANOVA, *p<0.05 (Bonferroni).

Example 4

Figure 6A:
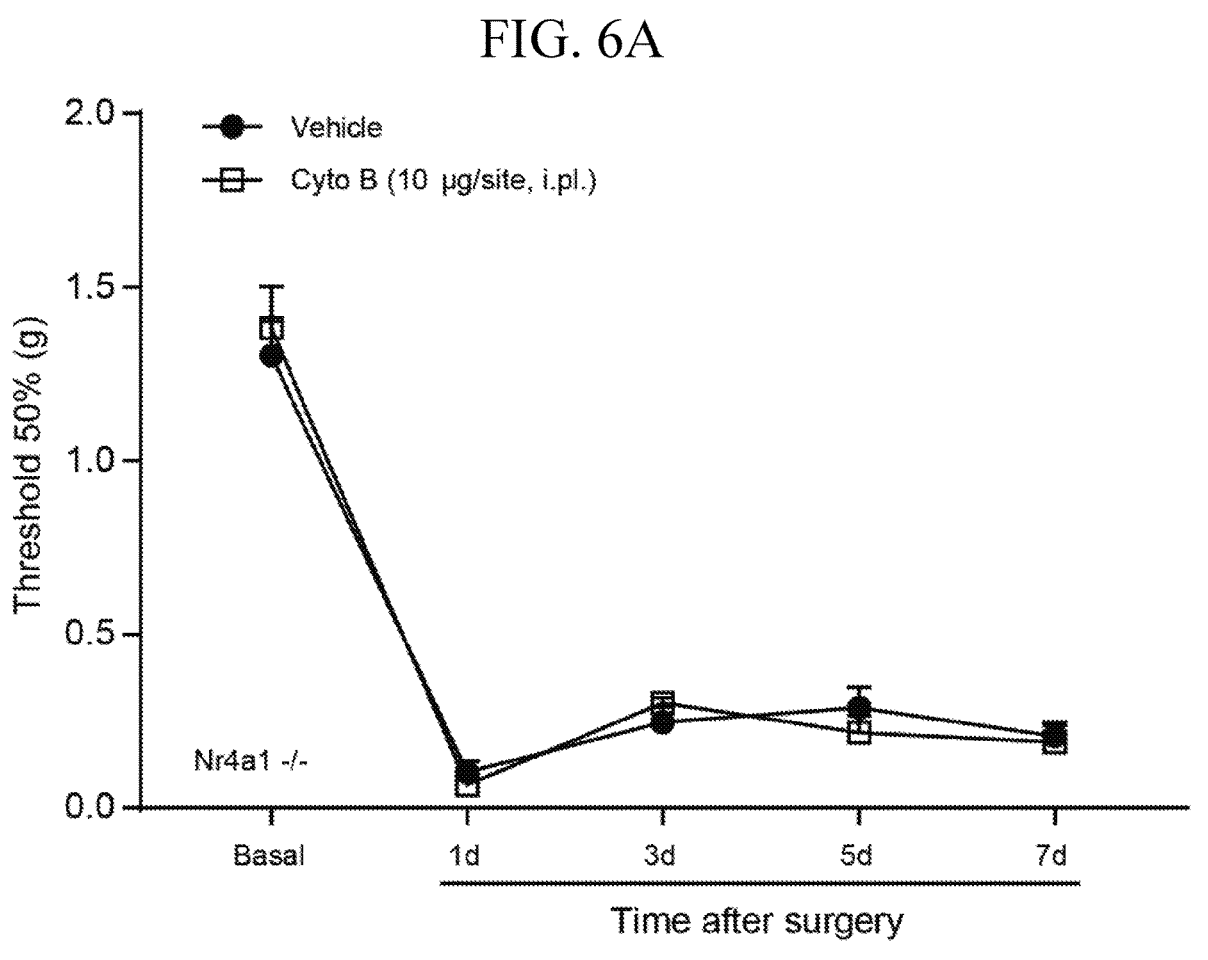
Figure 6B:
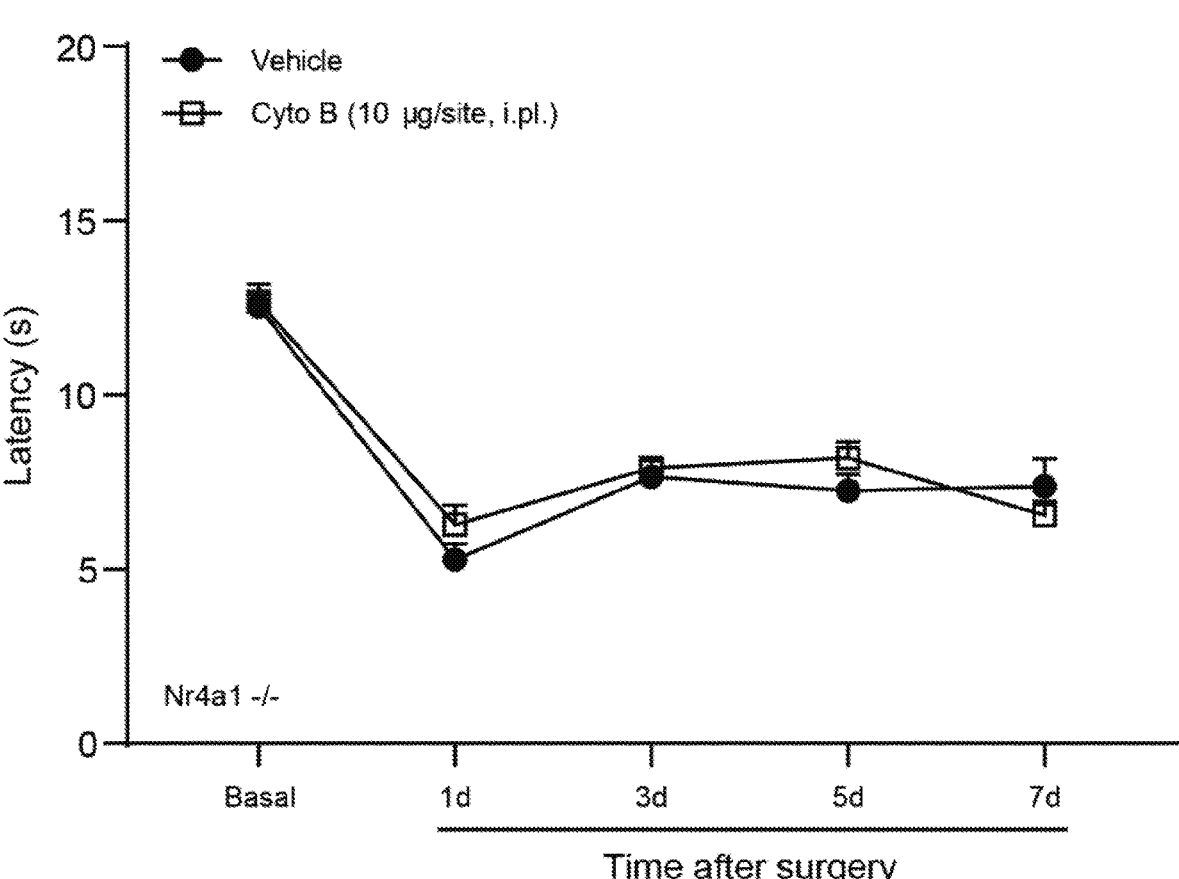

An experiment was conducted to show that an NA4A1 agonist decreases the expression levels of pro-inflammatory mediators in cultured macrophages. FIGS. 6A and 6B are graphs showing that local injection of NA4A1 agonist fails to resolve postoperative pain in NR4A1 knockout male mice. FIG. 6A is a graph showing mechanical hypersensitivity as assessed by von Frey filaments, and FIG. 6B is a graph showing thermal hypersensitivity as assessed by Hargreaves test. Cytosporone B (Cyto B) or vehicle control were administered by intraplantar injections. n=5 male mice per group, Two-way ANOVA, *p<0.05 (Bonferroni).

Example 5

Figure 7A:
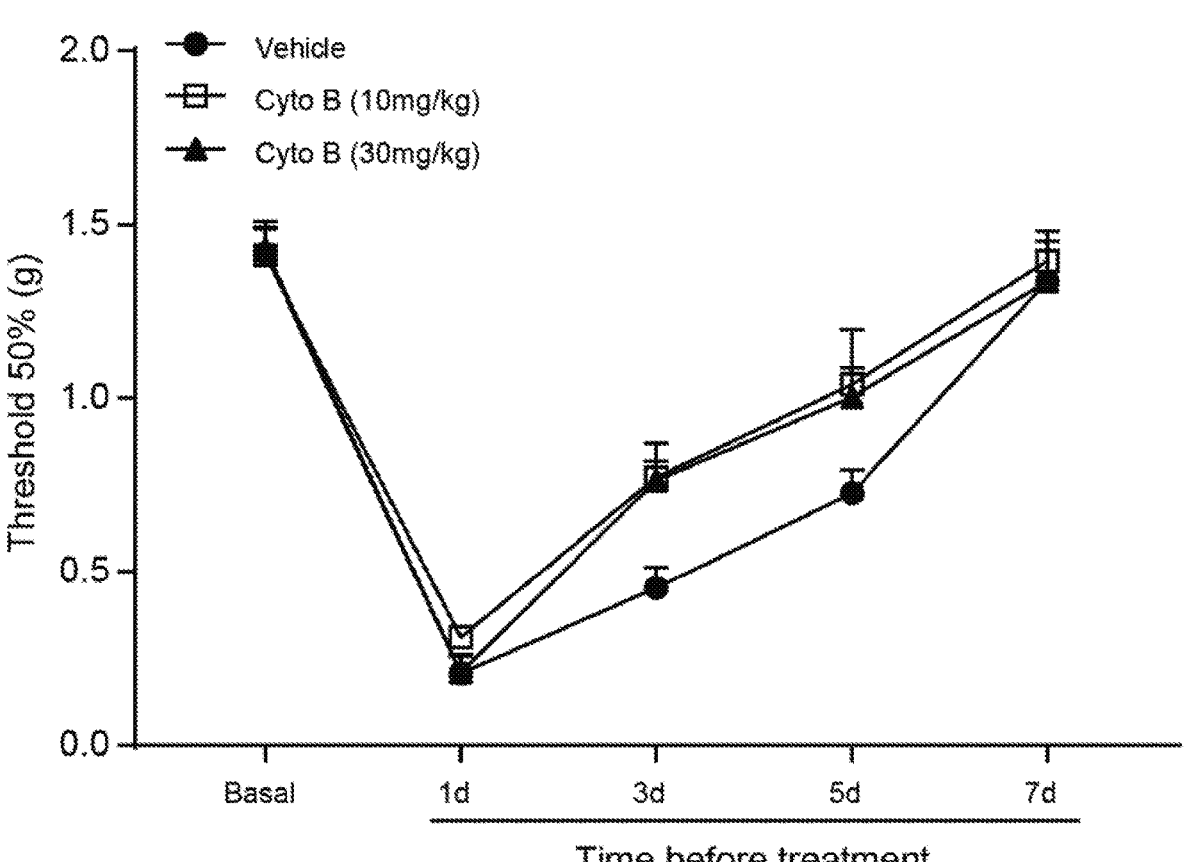
FIGS. 7A and 7B are graphs showing that systemic injection of NA4A1 agonist has limited effects on postoperative pain in male mice.
Figure 7B:
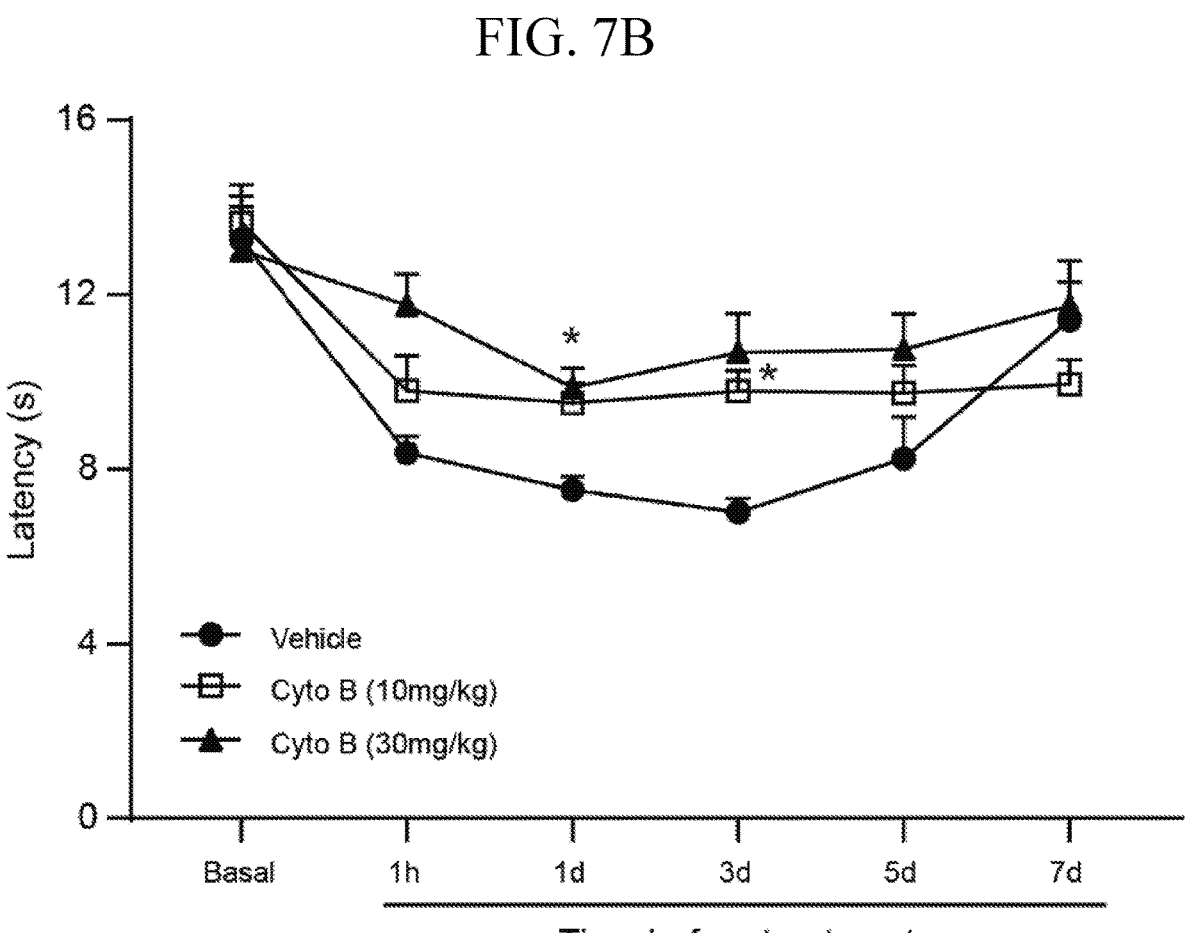

FIGS. 7A and 7B are graphs showing that systemic injection of NA4A1 agonist has limited effects on postoperative pain in male mice. FIG. 7A is a graph showing mechanical hypersensitivity as assessed by von Frey filaments. FIG. 7B is a graph showing thermal hypersensitivity as assessed by Hargreaves test. Cytosporone B (Cyto B) or vehicle control were administered by intraperitoneal injections. n=5 male mice per group, Two-way ANOVA, *p<0.05 (Bonferroni).

Figure 8:
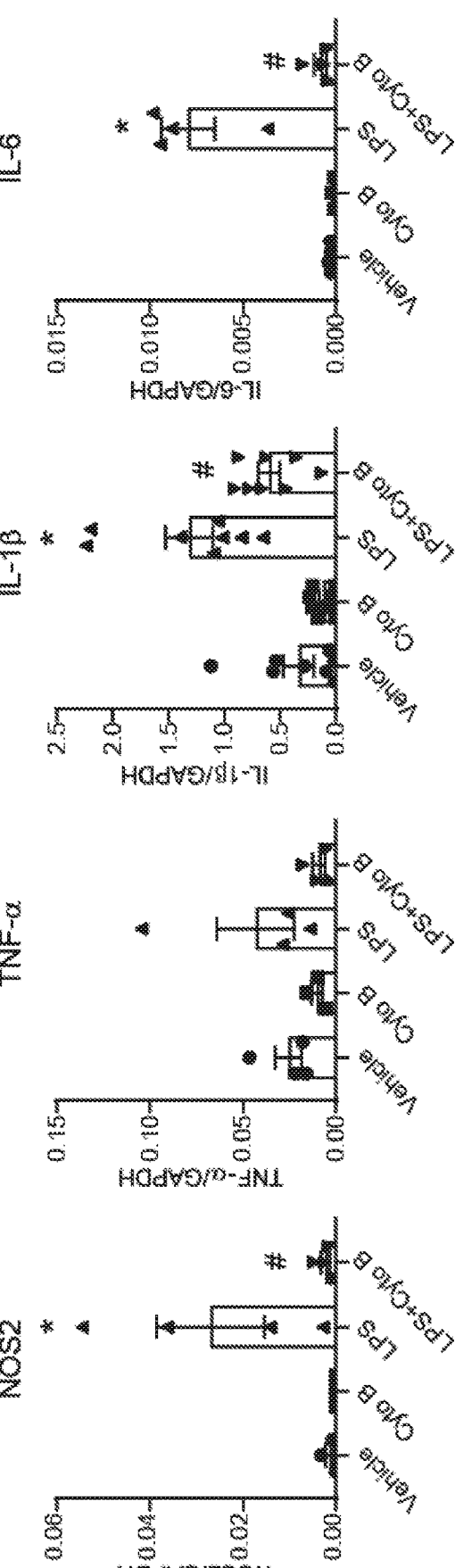
FIG. 8 is a series of graphs showing that NA4A1 agonist decreases the expression of pro-inflammatory mediators in macrophages. Peritoneal macrophages were cultured and incubated with vehicle control, cytosporone B (Cyto B, 10 µg/ml) or/and the macrophage activator lipopolysaccharide (LPS, 20 ng/ml). n=4-8 cultures per group, One-way ANOVA, *p<0.05 (Vehicle vs. LPS, Bonferroni), #p<0.05 (LPS VS. LPS+Cyto B, Bonferroni).

FIG. 8 is a series of graphs showing that NA4A1 agonist decreases the expression of pro-inflammatory mediators in macrophages. Peritoneal macrophages were cultured and incubated with vehicle control, cytosporone B (Cyto B, 10 μg/ml) or/and the macrophage activator lipopolysaccharide (LPS, 20 ng/ml). n=4-8 cultures per group, One-way ANOVA, *p<0.05 (Vehicle vs. LPS, Bonferroni), #p<0.05 (LPS VS. LPS+Cyto B, Bonferroni).

Example 6

Figure 9A:
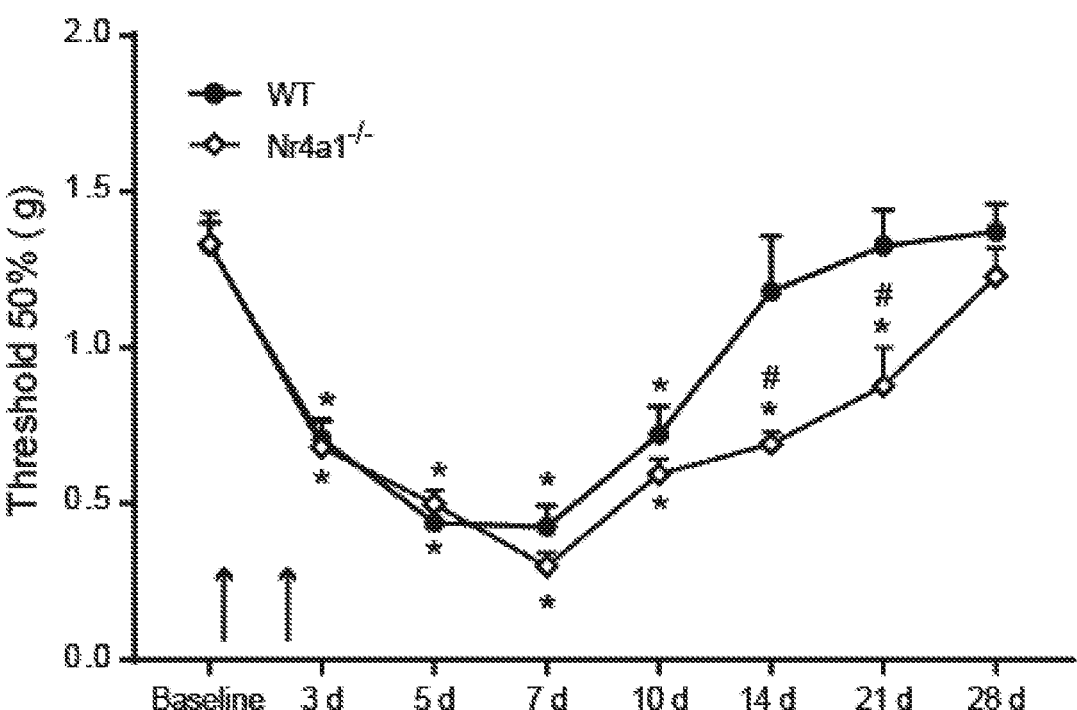
FIGS. 9A and 9B are graphs showing that NA4A1 deficiency exacerbates chemotherapy-induced neuropathic pain and neuroinflammation in DRG tissue.
Figure 9B:
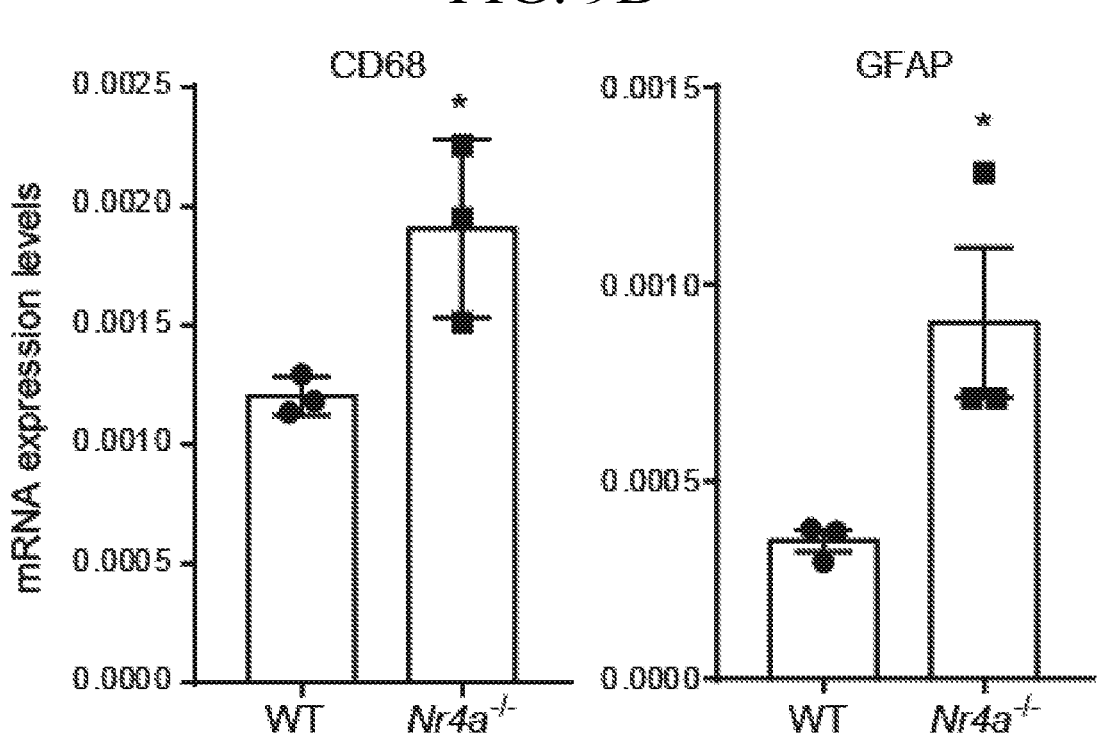

We used mouse and human tissues and a well-characterized mouse model of CINP consisting of repeated injection of the chemotherapeutic drug paclitaxel to show that: NR4A1 is expressed in mouse and human DRGs, mice lacking NA4A1 develop excessive mechanical allodynia and neuroinflammation in DRGs. FIGS. 9A and 9B are graphs showing that NR4A1 deficiency exacerbates chemotherapy-induced neuropathic pain and neuroinflammation in DRG tissue. FIG. 9A shows the time course of mechanical allodynia induced by 2 injections of paclitaxel (2 mg/kg, every other day and indicated by arrows) in wild-type (WT) and Nr4a1-/- mice. n=5 male mice per group, Two-way ANOVA, *p<0.05 compared to baseline and #P<0.05 compared to WT (Bonferroni). FIG. 9B shows the expression levels measured by real-time RT-PCR of neuroinflammatory markers CD68 and GFAP, in DRGs examined on day 14 after paclitaxel treatment. n=3 samples per group, *P<0.05 (t-test) compared to WT.

Example 7

Figure 10A:
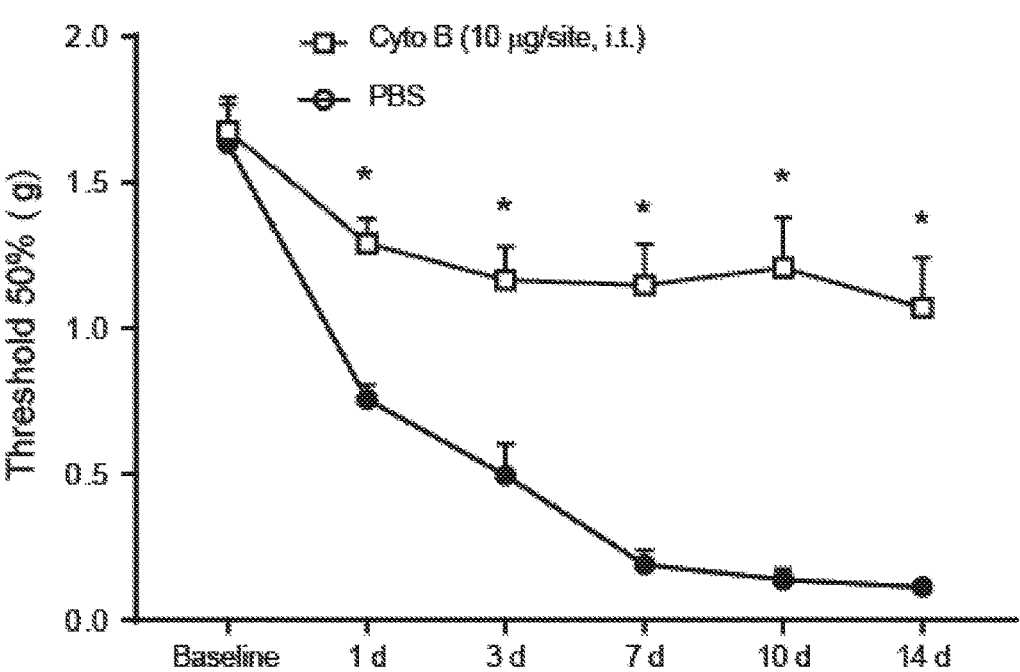
FIGS. 10A and 10B are graphs showing that NA4A1 activation by Cytosporone B (Csn-B) prevents and reverses chemotherapy induced neuropathic pain.
Figure 10B:
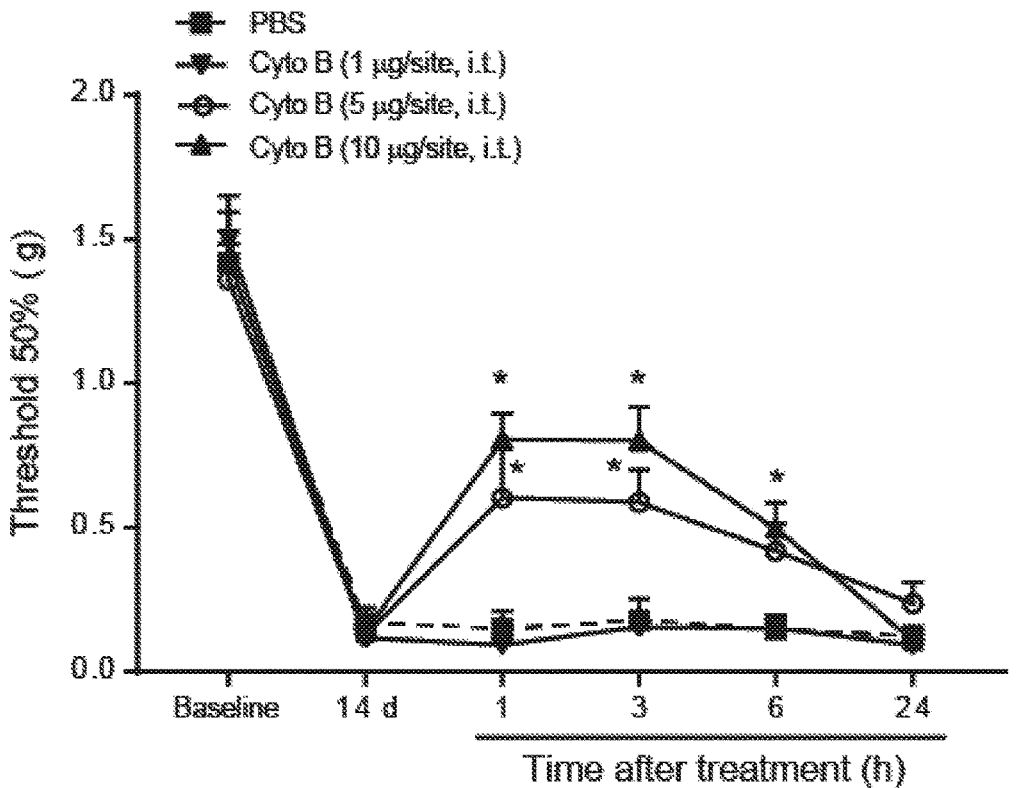

In another experiment, we found that local delivery of the NA4A1 agonist Cytosporone B significantly prevent and reverse mechanical allodynia in mice. FIGS. 10A and 10B are graphs showing that NA4A1 activation by Cytosporone B (Csn-B) prevents and reverses chemotherapy induced neuropathic pain. FIGS. 10A and 10B are graphs showing that NR4A1 activation by Cytosporone B (Csn-B) prevents and reverses chemotherapy induced neuropathic pain. FIG. 10A shows the time course of mechanical allodynia induced by 4 systemic injections of paclitaxel (2 mg/kg, every other day) in wild-type (WT) with or without Csn-B, which was delivered intrathecally (i.t.) at the as the paclitaxel. n=5 male mice per group, Two-way ANOVA, *p<0.05 compared to vehicle control phosphate buffered saline (PBS) (Bonferroni). FIG. 10B shows the time course of mechanical allodynia in wild-type (WT) with or without Csn-B. Treatments were delivered 14 d after the first delivery of paclitaxel (same delivery protocol as in A) to assess the reversal effect of different doses of Csn-B. n=5 male mice per group, Two-way ANOVA, *p<0.05 compared to vehicle control phosphate buffered saline (PBS) (Bonferroni).

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of"

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of treating pain in a patient having postoperative pain or chemotherapy induced neuropathic pain, the method comprising:
   a. assessing the patient to determine if they are experiencing post-operative pain or chemotherapy induced neuropathic pain, and if such pain is diagnosed;
   b. administering to the patient a therapeutically effective amount of an agonist for the nuclear receptor subfamily 4, group A, member 1 (NR4A1), wherein the agonist is Cytosporone B.

2. The method of claim 1 wherein the patient is administered repeated doses of the agonist.

3. The method of claim 1 wherein the patient is diagnosed with post-operative pain.

4. The method of claim 3 wherein the agonist is administered by local injection.

5. The method of claim 3 wherein the agonist is administered systemically.

6. The method of claim 1 wherein the patient is diagnosed with chemotherapy induced neuropathic pain.

7. The method of claim 6 wherein the agonist is administered by local injection.

8. The method of claim 6 wherein the agonist is administered systemically.

9. A method of preventing pain in a patient who is at risk of developing pain, the method comprising:

a. assessing the patient to determine if they are at risk of developing pain from a preexisting condition, and if such risk is diagnosed;

b. administering to the patient a therapeutically effective amount of an agonist for the nuclear receptor subfamily 4, group A, member 1 (NR4A1), wherein the agonist is Cytosporone B.

10. The method of claim 9 wherein the preexisting condition is selected from the group consisting of previous surgeries, genetic modifications, diseases, psychological state, and combinations thereof.

11. The method of claim 9 further comprising administering a chemotherapeutic drug to the patient, wherein the agonist is administered in combination with the chemotherapeutic drug.

12. The method of claim 11 wherein the chemotherapeutic drug is paclitaxel.

\* \* \* \* \*